US006652463B2

(12) United States Patent
Hunt et al.

(10) Patent No.: US 6,652,463 B2
(45) Date of Patent: Nov. 25, 2003

(54) SYSTEM AND METHOD FOR NON-LINEAR DETECTION OF ULTRASONIC CONTRAST AGENTS AT A FUNDAMENTAL FREQUENCY

(75) Inventors: Thomas J. Hunt, Pelham, NH (US); Patrick G. Rafter, Windham, NH (US); George A. Brock-Fisher, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/282,452

(22) Filed: Oct. 29, 2002

(65) Prior Publication Data

US 2003/0060713 A1 Mar. 27, 2003

Related U.S. Application Data

(63) Continuation of application No. 09/616,510, filed on Jul. 14, 2000, now Pat. No. 6,497,665.

(51) Int. Cl.$^7$ .................................................. A61B 8/00
(52) U.S. Cl. ...................................... 600/458; 600/443
(58) Field of Search ............................... 600/458, 443, 600/447, 440, 437, 441, 442

(56) References Cited

U.S. PATENT DOCUMENTS

| | | | |
|---|---|---|---|
| 5,456,257 A | | 10/1995 | Johnson et al. |
| 5,577,505 A | * | 11/1996 | Brock-Fisher et al. ....... 600/458 |
| 5,706,819 A | * | 1/1998 | Hwang et al. ............... 600/458 |
| 5,913,823 A | * | 6/1999 | Hedberg et al. ............. 600/443 |
| 6,494,841 B1 | * | 12/2002 | Thomas et al. .............. 600/447 |
| 6,497,665 B1 | * | 12/2002 | Hunt et al. .................. 600/458 |

* cited by examiner

Primary Examiner—Francis J. Jaworski
Assistant Examiner—Ruby Jain
(74) Attorney, Agent, or Firm—John Vodopia (57) ABSTRACT

A system and method for fundamental real-time imaging of the non-linear response of tissue perfused with a contrast agent are disclosed. An image with increased sensitivity to non-linear responses can be achieved by detecting the ultrasound response at the fundamental frequency from tissue perfused with a contrast agent and excited by multiple excitation levels. The responses detected from the multiple excitation levels may be gain corrected in an amount corresponding to the difference in magnitude of the excitation levels, then mathematically combined. The mathematical manipulation serves to remove linear responses to the fundamental excitation from the detected image. An ultrasonic contrast agent and tissue imaging system can be implemented with a transducer, first and second transmitters, a receiver, a control system, a processing system and a display. The transmitters generate electrical signals that are translated by the transducer into first and second pressure waves respectively, the respective pressure waves being of different power magnitudes. A control system electrically coupled to the transmitters, the transducer, and a receiver, coordinates pressure wave transmissions and the reception of ultrasonic responses. A processing system removes linear responses leaving the non-linear responses from the contrast agent and the surrounding tissue. Lastly, a display configured to receive the non-linear response creates an image of the insonified contrast agent and surrounding tissue.

33 Claims, 7 Drawing Sheets

SYSTEM AND METHOD FOR NON-LINEAR DETECTION OF ULTRASONIC CONTRAST AGENTS AT A FUNDAMENTAL FREQUENCY

CROSS REFERENCE TO RELATED APPLICATIONS

This is a continuation of application Ser. No. 09/616,510, filed Jul. 14, 2000 now U.S. Pat. No. 6,497,665.

FIELD OF THE INVENTION

The present disclosure relates to ultrasonic imaging. More particularly, the invention relates to a system and method for fundamental imaging of the non-linear response of tissue perfused with a contrast agent.

BACKGROUND OF THE INVENTION

Ultrasonic imaging has quickly replaced conventional X-rays in many clinical applications because of image quality, safety, and low cost. Ultrasonic images are typically formed through the use of phased or linear array transducers which are capable of transmitting and receiving pressure waves directed into a medium, such as the human body. Such transducers normally comprise multielement piezo-electric materials, which vibrate in response to an applied voltage to produce the desired pressure waves.

To obtain high quality images, the transducer is constructed so as to produce specified frequencies of pressure waves. Generally speaking, low frequency pressure waves provide deep penetration into the medium (e.g., the body), but produce poor resolution images due to the length of the transmitted wavelengths. On the other hand, high frequency pressure waves provide high resolution, but with poor penetration. Accordingly, the selection of a transmitting frequency has involved balancing resolution and penetration concerns. Unfortunately, resolution has suffered at the expense of deeper penetration and vice versa. Traditionally, the frequency selection problem has been addressed by selecting the highest imaging frequency (i.e., best resolution) which offers adequate penetration for a given application. For example, in adult cardiac imaging, frequencies in the 2 MHz to 3 MHz range are typically selected in order to penetrate the chest wall. Lower frequencies have not been used due to the lack of sufficient image resolution. Higher frequencies are often used for radiology and vascular applications where fine resolution is required to image small lesions and arteries affected by stenotic obstructions.

Recently, new methods have been studied in an effort to obtain both high resolution and deep penetration. One such method is known as "harmonic imaging." Harmonic imaging is grounded on the phenomenon that objects, such as human tissues, develop and return their own non-fundamental frequencies, i.e., harmonics of the fundamental frequency. This phenomenon and increased image processing capabilities of digital technology, make it is possible to excite an object to be imaged by transmitting at a low (and therefore deeply penetrating) fundamental frequency ($f_o$) and receiving reflections at a higher frequency harmonic (e.g., $2f_o$) to form a high resolution image of an object. By way of example, a wave having a frequency less than 2 MHz can be transmitted into the human body and one or more harmonic waves having frequencies greater than 3 MHz can be received to form the image. By imaging in this manner, deep penetration can be achieved without a concomitant loss of image resolution.

Harmonic imaging can be particularly effective when used in conjunction with contrast agents. In contrast agent imaging, gas or fluid filled micro-sphere contrast agents are typically injected into a medium, normally the bloodstream. Because of their strong non-linear response characteristics when insonified at particular frequencies, contrast agent resonation can be easily detected by an ultrasound transducer. More specifically, a second harmonic response occurs when a contrast agent under ultrasonic pressure "maps" energy into the harmonics of the incident pressure waves, instead of the fundamental. Various non-linear detection schemes take advantage of the fact that contrast agents produce non-linear responses of a greater magnitude than the surrounding tissue. By using harmonic imaging after introducing contrast agents, medical personnel can enhance imaging capability for diagnosing the health of blood-filled tissues and blood flow dynamics within a patient's arterial system. For example, contrast agent harmonic imaging is especially effective in detecting myocardial boundaries, assessing microvascular blood flow, and detecting myocardial perfusion. Transducers have been designed for transmit frequencies in the range of 2 MHz to 3 MHz for sufficient resolution of cardiac valves, endocardial borders and other cardiac structures.

The power or mechanical index of the impinging ultrasound signal directly affects the contrast agent acoustical response. At lower powers, microbubbles resonate and emit harmonics of the transmitted frequency. The magnitude of these microbubble harmonics depends on the magnitude of the excitation signal pulse. At higher acoustical powers, microbubbles rupture and emit strong broadband signals.

A prior art diagnostic system, disclosed by Johnson et al. in U.S. Pat. No. 5,456,257, teaches improved imaging by introducing coated microbubble contrast agents in the body of a patient. The '257 patent further teaches destroying the contrast agents with ultrasonic energy and detecting the microbubble destruction through phase insensitive detection and differentiation of echoes received from consecutive ultrasonic transmissions.

SUMMARY OF THE INVENTION

The present invention relates to a system and method for real-time imaging of tissue perfused with a contrast agent. An image with increased sensitivity to non-linear responses, can be achieved by detecting the ultrasound response at the fundamental frequency from tissue perfused with a contrast agent and excited by multiple excitation levels. Briefly described, in architecture, an ultrasonic contrast agent and tissue imaging system can be implemented with a transducer, first and second transmitters, a receiver, a control system, a processing system and a display. The ultrasonic contrast agent and tissue imaging system may be configured such that the first and second transmitters generate first and second electrical signals that are translated by the transducer into first and second pressure waves respectively, the respective pressure waves being of different magnitudes. A control system electrically coupled to the first and second transmitters, the transducer, and a receiver coordinates pressure wave transmissions and the reception of ultrasonic responses from the insonified contrast agent and tissue. A processing system electrically coupled to the receiver processes the multiple responses in a manner such that linear responses are removed leaving the non-linear responses from the contrast agent and the surrounding tissue. Lastly, a display configured to receive the non-linear response creates an image of the insonified contrast agent and surrounding tissue.

The present invention can also be viewed as providing one or more methods for non-linear ultrasonic response signal detection. In this regard, one such method can be broadly summarized by the following steps: introducing a contrast agent into the tissue targeted for imaging; insonifying the tissue at a first intensity to generate a first response; insonifying the tissue at a second intensity, wherein the second intensity is different from the first, to generate a second response; separately measuring the first and second responses at the fundamental frequency; generating a projected response from the first response; and mathematically manipulating the projected response and the second response to derive the non-linear response.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

Having summarized various aspects of the present invention, reference will now be made in detail to the description of the invention as illustrated in the drawings. While the invention will be described in connection with these drawings, there is no intent to limit it to the embodiment or embodiments disclosed therein. On the contrary, the intent is to cover all alternatives, modifications and equivalents included within the spirit and scope of the invention as defined by the appended claims. Turning now to the drawings, wherein like referenced numerals designate corresponding parts throughout the drawings, reference is made to FIG. 1, which illustrates a block diagram of an ultrasound imaging system 100 capable of multiple level ultrasound insonification. An example of an ultrasound imaging system 100 for producing a series of ultrasonic pulses with multiple excitation levels is disclosed in U.S. Pat. No. 5,577,505 which shares a common assignee with the present application and the contents of which are incorporated herein in their entirety.

Figure 1:
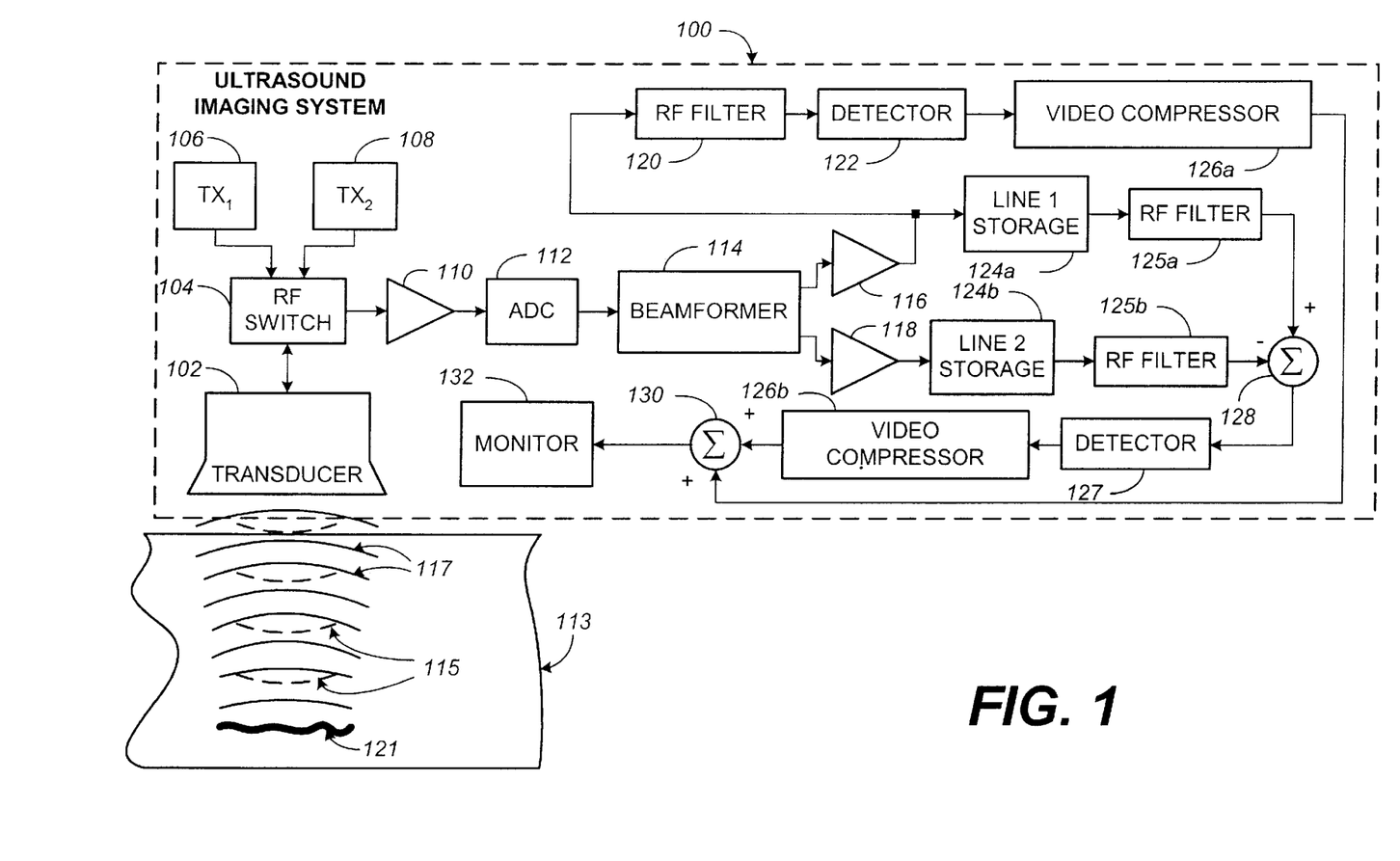
FIG. 1 is a block diagram of an ultrasound imaging system capable of multiple level ultrasound insonification.

In this regard, the ultrasound imaging system 100 may comprise a transducer 102, a radio-frequency (RF) switch 104, at least two transmitters 106, 108 (two shown), a time gain control amplifier 110, an analog to digital converter (ADC) 112, a beamformer 114, a first amplifier 116, a second amplifier 118, a RF filter 120, a first detector 122, a line 1 storage and a line 2 storage 124a, 124b, a line 1 RF filter and a line 2 RF filter 125a, 125b, a first video compressor 126a, a second video compressor 126b, a process signal detector 127, a first accumulator 128, a second accumulator 130, and a monitor 132. The transducer 102 may be electrically coupled to RF switch 104. The RF switch 104 may be configured as shown with two or more transmit inputs coupled to a first transmitter 106 and a second transmitter 108. The output of RF switch 104 may be electrically coupled to the time gain control amplifier 110. The RF switch 104 may be further configured with an output coupled to the time gain control amplifier 110. The time gain control amplifier 110 may be coupled to an ADC 112 before forwarding the response signals to a beamformer 114. The beamformer 114 may be coupled to a first amplifier 116 and a second amplifier 118. The first amplifier 116 may be further coupled to a RF filter 120, a first detector 122, and a first video compressor 126a, as well as, a line 1 storage 124a and a line 1 RF filter 125a. The second amplifier 118 may be coupled to a line 2 storage 124b, which may be further coupled to a line 2 RF filter 125b. Output signals from both the line 1 and the line 2 RF filters 125a, 125b may be electrically coupled with a first accumulator 128. The output from the first accumulator 128 may be electrically coupled to a process signal detector 127 and a second video compressor 126b before being forwarded to a second accumulator 130. The second accumulator 130 may be configured to receive output signals from both the first and second video compressors 126a, 126b and to supply an input signal to monitor 132.

The RF switch 104 isolates the transmitter portion of the ultrasound imaging system 100 from the receiver portion. The multi-transmitter architecture illustrated in FIG. 1 allows for variable power levels between transmit events (ultrasound lines), which are further illustrated in FIG. 1 by ultrasound lines 115. When the ultrasound lines 115 encounter a tissue layer 113 that is receptive to ultrasound insonification the multiple transmit events or ultrasound lines 115 penetrate the tissue layer 113. As long as the magnitude of the multiple ultrasound lines exceeds the attenuation affects of the tissue layer 113, the multiple ultrasound lines 115 will reach an internal target 121. Those skilled in the art will appreciate that tissue boundaries or intersections between tissues with different ultrasonic impedances will develop ultrasonic responses at harmonics of the fundamental frequency of the multiple ultrasound lines 115. It will be further appreciated that tissue insonified with ultrasonic waves develops harmonic responses because the compressional portion of the insonified waveforms travels faster than the rarefactional portions. The different rates of travel of the compressional and the rarefactional portions of the waveforms causes the wave to distort producing an harmonic signal which is reflected or scattered back through the various tissue boundaries.

As further illustrated in FIG. 1, such harmonic responses may be depicted by ultrasonic reflections 117. It is significant to note that while FIG. 1 illustrates only a second harmonic response to the incident multiple ultrasound lines 115 impinging the internal target 121 other harmonic responses may also observed. As by way of example, it is known that subharmonic, harmonic, and ultraharmonic responses may be created at the tissue boundary between tissue layer 113 and the internal target 121, when the internal target has been perfused with one or more contrast agents. The internal target 121 alone will produce harmonic responses at integer multiples of the fundamental frequency. Various contrast agents on the other hand, have been shown to produce subharmonic, harmonic, and ultraharmonic responses.

Those ultrasonic reflections of a magnitude that exceeds that the attenuation affects from traversing tissue layer 113 may be monitored and converted into an electrical signal by the combination of the RF switch 104 and transducer 102. The electrical representation of the reflected ultrasonic reflections 117 may be received at the time gain control amplifier 110. The output of the time gain control amplifier 110 may be converted by ADC 112 into a digital representation of the various harmonic responses before being forwarded for further processing by the beamformer 114. The output of the beamformer 114 may be coupled to a first and second amplifier 116, 118. A gain for the first amplifier 116 may be adjusted as function of the voltage created by the first transmitter 106. The second amplifier 118 may be configured in proportion to the ratio of the voltages between the first transmitter 106 and the second transmitter 108. The output of time gain control amplifier 110 may be beamformed, filtered, and demodulated to In-phase (I) and Quadrature (Q) baseband signals in beamformer 114. Two line signals may then be stored in memory as illustrated in FIG. 1 by the line 1 storage 124a and the line 2 storage 124b. After gain adjustment in the first amplifier 116, the beamformed response signal may then be filtered in RF filter 120 and envelope detected in the first detector 122 prior to further processing by the first video compressor 126a. As further illustrated in FIG. 1, the line 1 reflection signal may be forwarded to the line 1 storage 124a and later filtered in the line 1 RF filter 125a, which may be configured to reduce or eliminate harmonic responses before forwarding the line 1 reflection signal to the first accumulator 128. Similarly, the line 2 reflection signal may be forwarded to the line 2 storage 124b and later filtered in the line 2 RF filter 125b, which may also be configured to eliminate harmonic responses before forwarding the line 2 reflection signal to the first accumulator 128. As illustrated in FIG. 1, the line 2 reflection signal may be subtracted from the line 1 reflection signal in accumulator 128. The output of the first accumulator 128 may then be processed by a process signal detector 127 before forwarding the detected difference between the line 1 and line 2 reflection signals to the second video compressor 126b. Both the first video processed reflection image and the second video processed reflection image may then be combined in the second accumulator 130 with both images being shown simultaneously via the monitor 132.

While the ultrasound imaging system 100 illustrated in FIG. 1 depicts mathematical combination in the first accumulator 128 of the non-linear response prior to signal detection, it will be apparent to those skilled in the art that the step of subtraction may be performed after detection. As by way of a non-limiting example, a RF domain subtraction may be performed by combining or adding a plurality of phase inverted pulses, then processing the residual signal through an envelope detector. Such a system is more sensitive to relative motion between the two responses than a system that performs envelope detection on a plurality of input signals prior to mathematically combining the input signals to derive the non-linear response.

Figure 2A:
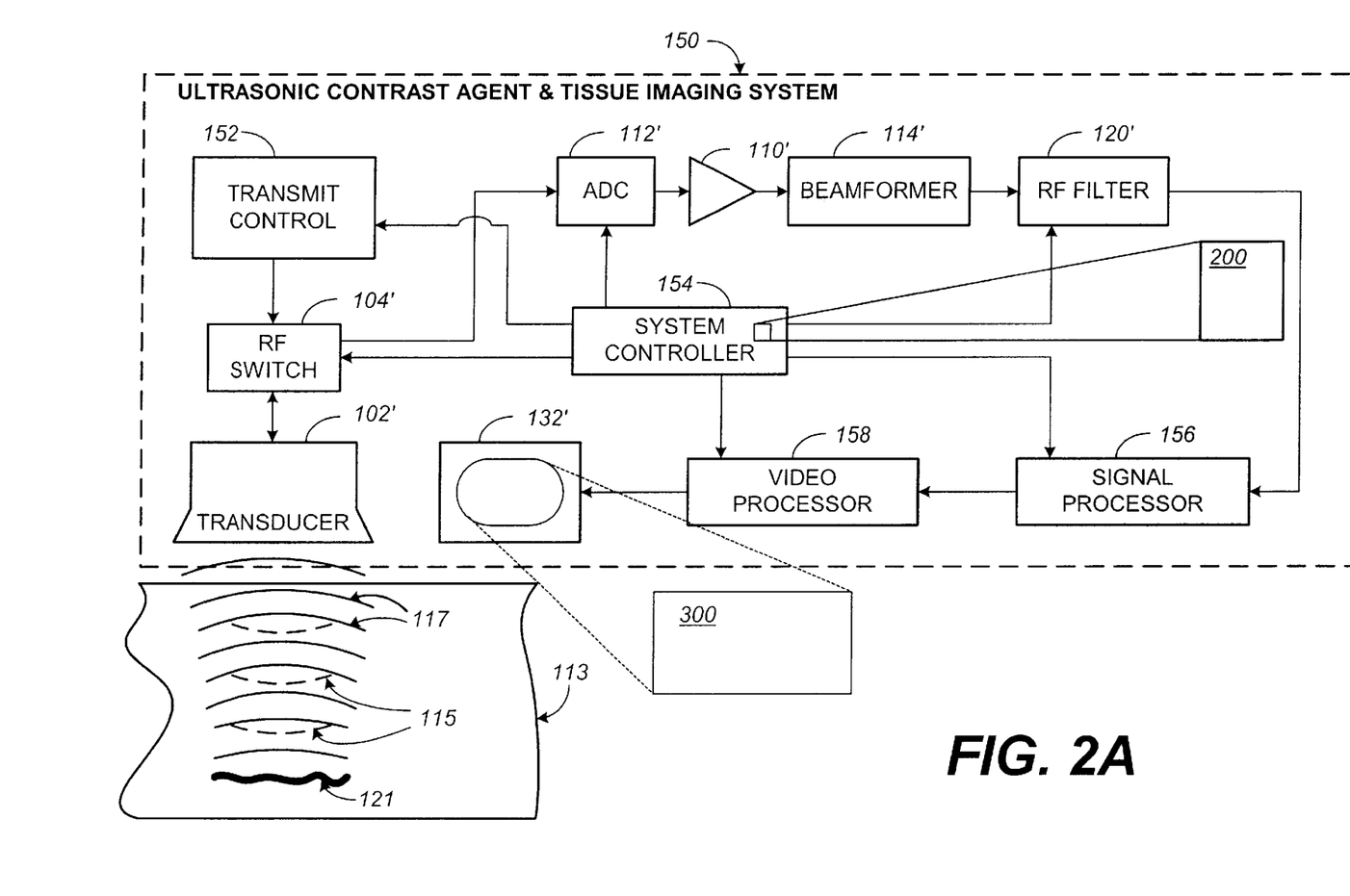
FIG. 2A is a block diagram of an ultrasonic contrast agent and tissue imaging system in accordance with the present invention.

Having described the architecture and operation of the ultrasound imaging system 100 of FIG. 1, attention is now directed to FIG. 2A, which illustrates a block diagram of an ultrasonic contrast agent and tissue imaging (UCATI) system in accordance with the present invention.

In this regard, the UCATI system 150 may comprise a transducer 102', a RF switch 104', a transmit control 152, a system controller 154, an analog to digital converter (ADC) 112', a time gain control amplifier 110', a beamformer 114', a RF filter 120', a signal processor 156, a video processor 158, and a monitor 132'. The transducer 102' may be electrically coupled to RF switch 104'. The RF switch 104' may be configured as shown with a transmit input coupled to the transmit control 152 and a transducer port electrically coupled to the transducer 102'. The output of the RF switch 104' may be electrically coupled to the ADC 112' before further processing by the time gain control amplifier 110'. The time gain control amplifier 110' may be coupled to a beamformer 114'. The beamformer 114' may be coupled to the RF filter 120'. The RF filter 120' may be further coupled to a signal processor 156 before further processing in the video processor 158. The video processor 158 may then be configured to supply an input signal to a monitor 132'. The system controller 154 may be coupled to the RF switch 104', the transmit control 152, the ADC 112', the RF filter 120', and both the signal processor 156 and the video processor 158 to provide necessary timing signals to each of the various devices.

As will be appreciated by persons having ordinary skill in the art, the system controller 154 can include one or more processors, computers, and other hardware and software components for coordinating the overall operation of the UCATI system 150. In addition, it will be appreciated that the system controller 154 may include software which comprises an ordered listing of executable instructions for implementing logical functions, which can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. The computer readable medium can be, for instance, an electronic, magnetic, optical, electromagnetic, infrared, or semiconductor system, apparatus, device, or propagation medium. Such a list of executable instructions is further illustrated in FIG. 2A as a method for ultrasonic imaging 200, which will be further explained in connection with FIG. 2B.

The RF switch 104' isolates the plurality of transmit signals that may be generated and distributed by transmit control 152 from the ultrasonic response receiving and processing sections comprising the remaining elements illustrated in FIG. 2A. The system architecture illustrated in FIG. 2A provides a plurality of electronic transmit signals that may be converted by the transducer 102' to one or more ultrasonic pressure waves herein illustrated by ultrasound lines 115. Those ultrasonic reflections of a magnitude that exceeds that the attenuation affects from traversing tissue layer 113 may be monitored and converted into an electrical signal by the combination of the RF switch 104' and transducer 102'. The electrical representation of the reflected ultrasonic reflections 117 may be received at the ADC 112' where they are converted into a digital signal. The time gain control amplifier 110' coupled to the output of the ADC 112' may be configured to adjust amplification in relation to the total time a particular ultrasound line needed to traverse the tissue layer 113. In this way, response signals from one or more internal targets 121 will be gain corrected so that ultrasonic reflections 117 generated from relatively shallow objects do not overwhelm, in magnitude, ultrasonic reflections 117 generated from insonified objects further removed from the transducer 102'.

The output of the time gain control amplifier 110' may be beamformed, filtered and demodulated via the beamformer 114', the RF filter 120', and the signal processor 156. The processed response signal may then be forwarded to the video processor 158. The video version of the response signal may then be forwarded to monitor 132' where an ultrasound image 300 may be viewed. It will be further appreciated by those of ordinary skill in the art that the UCATI system 150 of the present invention may be configured to produce one or more images and or oscilloscopic traces along with other tabulated and or calculated information that would be useful to the operator.

Figure 2B:
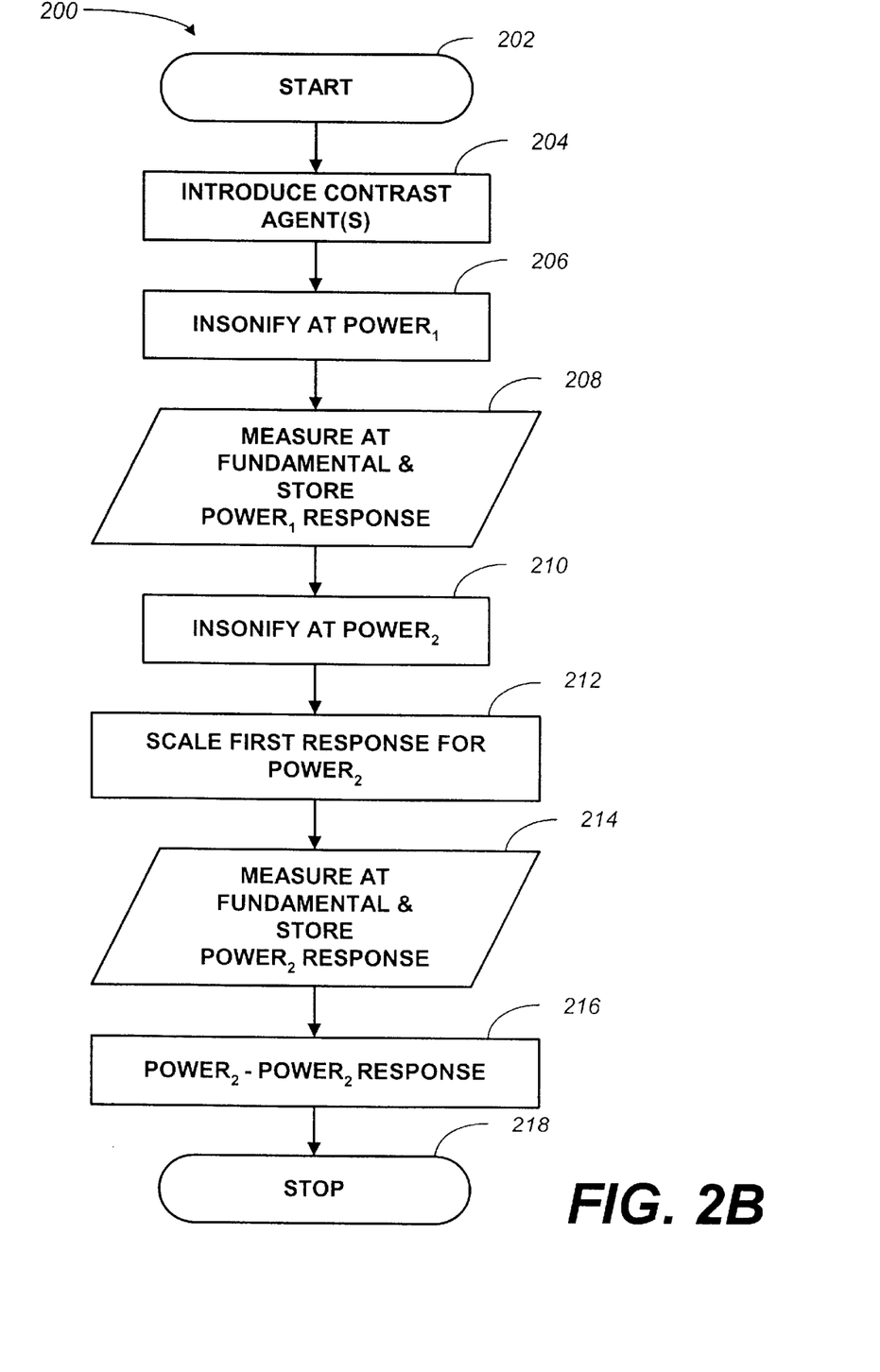
FIG. 2B is a flowchart illustrating a diagnostic method for creating an image with increased sensitivity using the ultrasound imaging system of FIG. 2A.

Having described the architecture of the UCATI system 150 of the present invention, attention is now directed to FIG. 2B, which illustrates a flowchart depicting a corresponding method that may be performed by the UCATI system 150 of FIG. 2A.

In this regard, a method for ultrasonic imaging 200 of one or more contrast agents begins with step 202 designated "start." In step 204, a patient may be treated with one or more contrast agents. As will be further explained in relation to FIGS. 3–5, contrast agents may be introduced into the bloodstream of a patient in order to enhance an ultrasonic image 300 of portions of the circulatory system of the patient. After introducing the one or more contrast agents in step 204 and waiting for an appropriate amount of time, the UCATI system 150 of FIG. 2A may be configured to insonify tissue targeted for observation at a first power level as illustrated in step 206. Next, in step 208, the UCATI system 150 may be configured to measure, process, and record the non-linear response at the fundamental frequency to the first transmit event or ultrasound reflection 117 initiated by the ultrasound wave introduced in step 206.

Next, in step 210, the method for ultrasound imaging 200 continues by insonifying the tissue targeted for observation at a second power level. In step 212, the UCATI system 150 scales the first non-linear response to the first ultrasound reflection 117 for the second power level of step 210 to create a projected response. Next, in step 214, the UCATI system 150 may be configured to measure, process, and record the non-linear response at the fundamental frequency to the second transmit event or ultrasound reflection 117 initiated by the ultrasound wave introduced in step 210. In step 216, the projected response may be subtracted from the stored second response to determine the non-linear response due to the one or more contrast agents introduced in step 204. Any linear responses from both the surrounding tissue and the one or more contrast agents will be removed by step 216, leaving the non-linear responses of both the tissue and the one or more contrast agents for display by monitor 132' of the UCATI system 150 (see FIG. 2A). Last, the method for ultrasound imaging 200 may perform step 218, designated "stop."

It is significant to note that while the above description discloses ultrasonic response measurement at the fundamental frequency the transmit and receive portions of the UCATI system 150 may be matched in terms of bandwidth or a time domain impulse response. Using a matched receiver for measuring the ultrasonic responses has the principal advantage of providing maximum sensitivity as an imaging modality based at the fundamental frequency is subject to less attenuation than an imaging modality that measures harmonic responses. A further advantage of measuring ultrasonic responses at the fundamental frequency is that a transducer 102' (see FIG. 2A) need only have adequate sensitivity at the fundamental frequency. A third advantage of using a matched receiver is that the contrast agent response is larger at the fundamental than at the harmonics.

While the contrast agent non-linear response is greatest at the fundamental frequency, particular contrast agent responses may be relatively close to the noise floor across the received signal bandwidth of the UCATI system 150. In order to minimize the introduction of residual artifacts from imperfect response signal cancellation that may result from the insonification of tissue and the one or more contrast agents with a plurality of transmit waveforms, it is important to verify that the various transmitted waveforms are closely matched. As by way of example, for pulse inverted waveforms T1 and T2, if it is determined that T1 has a peak-to-peak pressure difference of 0.4 and that T2 has a peak-to-peak pressure difference of 0.396, the matching may be expressed in decibels (dB) as shown below:

$$\text{matching(dB)} = 20\log_{10}\left(\frac{(.4-.396)}{.4}\right) = -40 \text{ dB} \qquad \text{Eq. 1}$$

As a result, for transmitted waveforms with a 1.0% difference in their magnitudes, the non-linear contrast agent response will have to be greater than both the noise floor of the system and above any residual artifact introduced by the imperfect mathematical cancellation of tissue response signals (tissue signal −40 dB in the example above), in order for the UCATI system 150 to detect and display the response.

There are at least a couple of benefits of imaging a contrast agent while not impinging the contrast agent with sufficient energy to destroy the contrast agent. First, images are easier to acquire. As by way of example, imaging with destruction of a contrast agent requires the sonographer to hold the imaging plane for multiple cardiac cycles without visual feedback—a very challenging task. Second, function of an organ of interest can be monitored over time. As by way of further example, the function of the heart may be observed. In other words, does the bloodstream carrying the one or more contrast agents indicate adequate blood flow through each of the chambers of the heart. Similarly, is the contrast between the blood-filled chambers and the various structures of the heart indicative of a wall motion abnormality.

It is important to note that method descriptions or blocks in the flow chart illustrated in FIG. 2B should be understood as representing modules, segments, or portions of code which include one or more executable instructions for implementing specific logical functions or steps in the process, and alternate implementations are included within the scope of the preferred embodiment of the present invention in which functions may be executed out of order from that shown or discussed, including substantially concurrently or in reverse order, depending on the functionality involved, as would be understood by those reasonably skilled in the art of the present invention.

The magnitude of ultrasonic reflections 117 that result from ultrasound insonification varies with transmitted power and is significantly different for human tissue than that for contrast agents. For example, contrast agents have been shown to exhibit a non-linear response generated as a function of incident pressure squared. Tissue generates non-linear ultrasonic responses, which are significantly smaller in magnitude than that for contrast agents particularly at lower transmit powers By taking advantage of the difference in magnitude of the non-linear responses to ultrasound insonification and focusing on the fundamental frequency, the ultrasound imaging method of the present invention permits real-time perfusion observation to be performed with low-cost narrow bandwidth transducers. The ultrasound imaging method of the present invention also allows the received or observation frequency to be selected anywhere within the bandwidth of the transducer. In addition, by detecting non-linear responses of contrast agents at the fundamental frequency, the present invention takes advantage of fact that contrast agent responses are greatest at the fundamental.

Harmonic imaging methods, on the other hand, require the received frequency to be at a harmonic (usually twice) of the fundamental or transmitted frequency, which typically forces both the transmit and receive frequencies to be located near the skirts of the transducer's bandwidth where the magnitude of ultrasonic transmissions and reflections is typically attenuated. It is further significant to note that imaging techniques that focus on harmonic responses are also adversely affected by the increased attenuation signal losses that result in traversing the various tissues of the human body at the higher frequency harmonics.

As used herein, power level relates to insonification or acoustic intensity. Mechanical index is one parameter used to measure acoustic intensity. Mechanical index is a United States Food and Drug Administration (FDA) regulated parameter defined as peak rarefactional pressure in Mpa divided by the square root of the center frequency in MHz. Current FDA regulations limit the mechanical index to a maximum of 1.9, after allowing for tissue related frequency dependent attenuation.

It is important to note that different contrast agents respond differently to various insonification and detection techniques. It is theorized that these different responses can be explained due to flexibility of the shell material used to encase the agent, the size distribution within the body, and the particular characteristics of the gas inside the shell. As a result, determining an effective mechanical index for a particular application is somewhat patient and agent specific. The mechanical index needs to be low enough to not destroy the contrast agent while maintaining a linear response signal from insonified tissue. On the other hand, the mechanical index needs to be high enough to overcome the effects of tissue attenuation at the fundamental frequency while initiating a non-linear response from the one or more contrast agents. Generally, a mechanical index from 0.05 to 0.5 will meet these requirements for a broad range of contrast agents starting from the most fragile to the more resilient.

As described earlier with regard to FIGS. 1 and 2A achieving different power levels in each of two or more transmit events or ultrasound lines 115 (see FIG. 1) may be accomplished in several different ways. A preferred method of achieving the different power settings is by varying the transmit voltage. Varying transmit voltage has the direct result of varying the pressure amplitude of the resultant transmitted ultrasound lines 115 (see FIG. 1). Alternatively, different power levels may be accomplished by controlling the size of the aperture of the transducer 102' (see FIG. 2A). The aperture size may be varied in the lateral or elevation dimensions by using a synthetic aperture methodology. The aperture may be divided into two or more groups with transmit ultrasound lines 115 being separately fired from each group. The subsequent reflected energy is then stored. The entire aperture is then used to transmit a second incident pressure wave with an increased energy level. The subsequent reflected energy is again stored. In this embodiment, the scaling step includes beamforming the response from the two or more smaller apertures and subtracting those results from the response due to excitation from the entire aperture to determine the non-linear response.

Another way of controlling transmitted power levels is to fire a subset of elements in the array and compare the scaled subset response to a response from the entire transducer array. This method should be performed in a manner to reduce and or minimize grating lobes that stem from undersampling the aperture and steering errors that result from assymetries about the center of the aperture.

A non-limiting example of a multi-pulse technique that fires three pulses is described below. The first pulse may be generated by firing the "even" numbered elements within transducer 102'. The second pulse may be generated by controllably firing all elements of the transducer 102'. The third pulse may be generated by firing the "odd" numbered elements. The response signal processing portion of the UCATI system 150 may be configured to mathematically combine a response from the first and third pulses for further mathematical manipulation with the second response signal. It is important to note that the selection of elements to form the various element subsets for the first and third pulses is not limited to "even" and "odd" numbered elements of the transducer element array. It will be appreciated by those skilled in the art that more than three pulses may be generated and fired to further extend a multi-pulse insonification and imaging technique.

The multi-pulse technique described above serves a couple of purposes. First of all, adjusting the transmitted power by firing a subset of elements reduces the transmit power while providing the same voltage level to each transmission. If the transmit waveforms are not properly scaled and inverted, or if the waveforms differ in their frequency content, undesired residual artifacts from imperfect tissue response signal cancellations may be introduced by the UCATI system 150. By matching the voltage level used to generate the various pulses, the UCATI system 150 of the present invention reduces any undesired tissue signals introduced by mathematically combining signal responses generated from ultrasonic transmissions of varying power levels. Transmit waveform power magnitude matching over a number of various levels of comparison across a received bandwidth of interest will serve to reduce residual tissue response signal artifacts that may result from transmit power mismatches.

A second important result from using the multi-pulse technique is that by mathematically combining the first pulse response with the third pulse response, motion of an organ of interest (i.e., the heart) is averaged, so that when the second pulse response is mathematically processed (i.e., subtracted) from the combination of the first and third pulse responses, motion is suppressed between the various pulses.

Yet another way of controlling the transmitted power levels is to use a phase inversion technique. Phase inversion techniques are well understood by those skilled in the art of ultrasonic imaging. The description of an ultrasonic imaging system capable of producing, detecting, and image processing ultrasonic responses that use phase inversion techniques need not be described to understand the present invention and need not be described herein. It is significant to note, however, that mathematical post-processing of detected response signals may vary based on the desired effect of the processing and the phase of the transmitted waveforms responsible for the response signals. By coordinating one or more of the phase, intensity and frequency content of multiple transmitted pulses with the applicable response processing, motion artifacts between pulses may be substantially reduced.

Another technique that may be used to vary the transmitted levels would be to take advantage of the beam shape of a pressure wave. Transmitted pressure waves have a reduced magnitude that varies with angular distance. As by way of a non-limiting example, if a pressure wave is transmitted at 0 degrees and the UCATI system 150 is configured to receive responses at 0.0 and at 0.25 degrees, the power received at 0.25 degrees will be lower since it is off the peak of the transmitted beam.

Furthermore, it is significant to note that the method for ultrasonic imaging 200 is suited to any insonification technique, which suppresses tissue signal responses at the fundamental frequency of a significant magnitude so that non-linear responses from a contrast image can be detected. The method for ultrasonic imaging 200 may be shown as a color overlay such as color flow, or as a B-mode gray scale image.

Figure 3A:
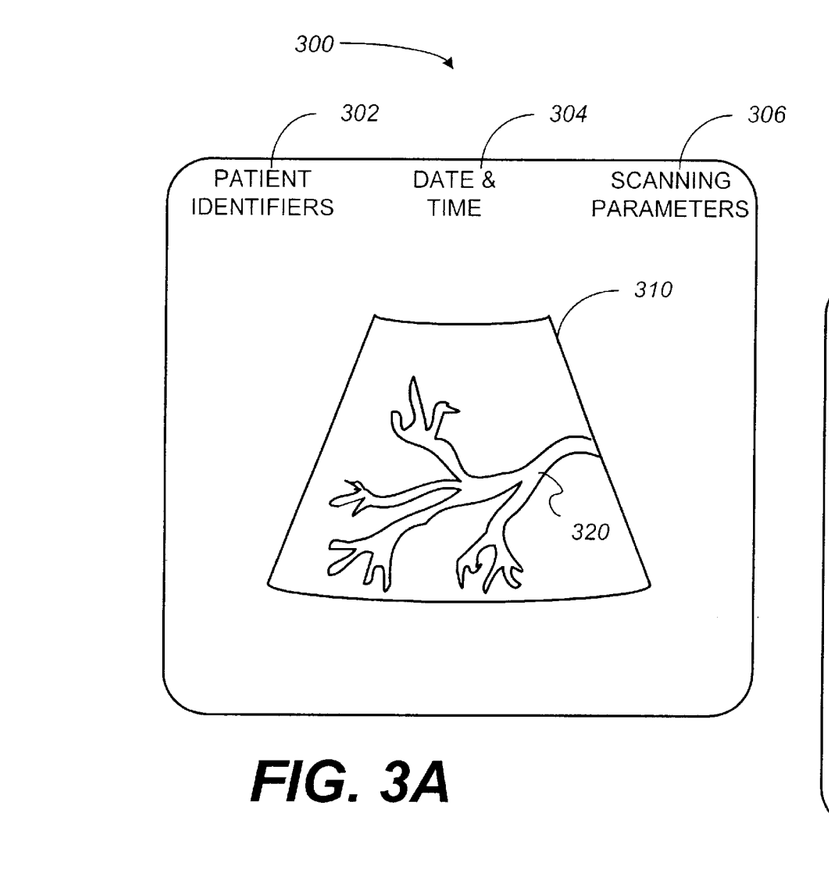
FIGS. 3A and 3B illustrate potential displays that might be generated by the ultrasound imaging system of FIG. 2A, when the image plane is focused on a portion of the circulatory system of a patient.
Figure 3B:
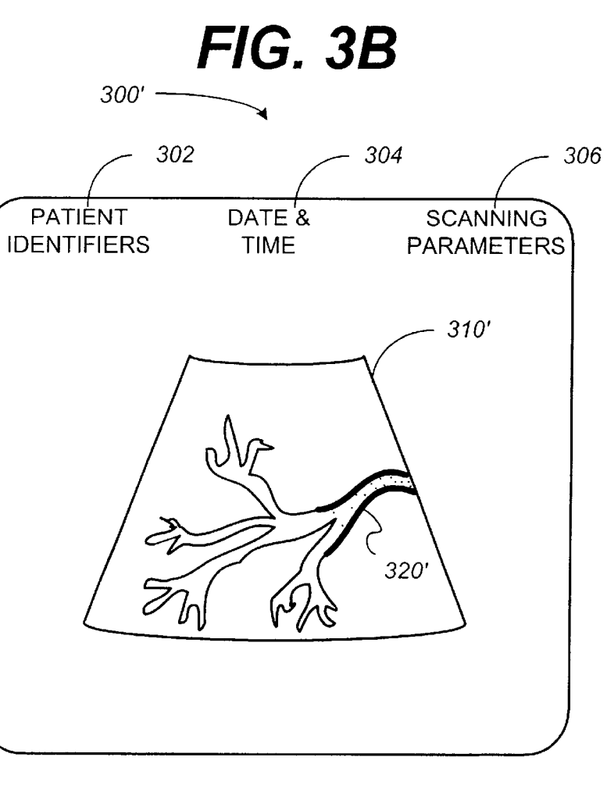

Having described a method for ultrasonic imaging 200 as illustrated in FIG. 2B attention is now directed to FIGS. 3A and 3B which illustrate potential displays that can be generated from the UCATI system 150 of FIG. 2A.

In this regard, ultrasound image 300 of FIG. 3A may comprise alphanumeric information in the form of patient identifiers 302, date and time identifiers 304 and scanning parameters 306. In addition to the one or more alphanumeric identifiers ultrasound image 300 may comprise a real-time ultrasound image display 310 of structure in a body such as a portion of the circulatory system 320. A real-time image may be used by a clinical technician to ascertain and locate an area of interest. Preferably the image is created from echoes returned from the non-destructive ultrasonic imaging of one or more contrast agents. FIG. 3B further illustrates ultrasound image 300', a snap-shot of a real-time ultrasound image display 310' of a portion of the circulatory system 320' after introduction of one or more contrast agents in the patient's bloodstream. As illustrated in FIG. 3B the non-linear response from the one or more contrast agents introduced into the bloodstream of the patient can have a significant effect on the contrast agent to tissue ratio in the ultrasound image 30' showing a portion of the circulatory system 320'. It is important to note that real-time contrast agent images may be acquired at any phase of the heart cycle, not just when the heart is predominately at rest. While the aforementioned real-time imagery of the heart is especially useful in cardiology, variations of this method may prove useful in radiology where anatomical structures are more stationary Having described two potential ultrasound images 300 and 300' with regard to FIGS. 3A and 3B, reference is now directed to FIGS. 4A and 4B, which illustrate a partially sectioned perspective view of a human heart. In this regard, the heart 400 comprises a right and left atrium 402, 406 and a right and left ventricle 404, 408 encompassed by a myocardial tissue layer 405, with a tricuspid valve 410 separating the right atrium 402 from the right ventricle 404 and a mitral valve 440 separating the left atrium 406 from the left ventricle 408. In addition, a pulmonary valve 420 separates the right ventricle 404 from the pulmonary arteries 417 and an aortic valve 430 separates the left ventricle 408 from the aorta 415. As further illustrated in FIG. 4A, a superior and inferior vena cava 411, 413 return blood from the body to the right atrium 402 and pulmonary veins 419 return blood from the lungs (not shown) to the left atrium 406.

Figure 4A:
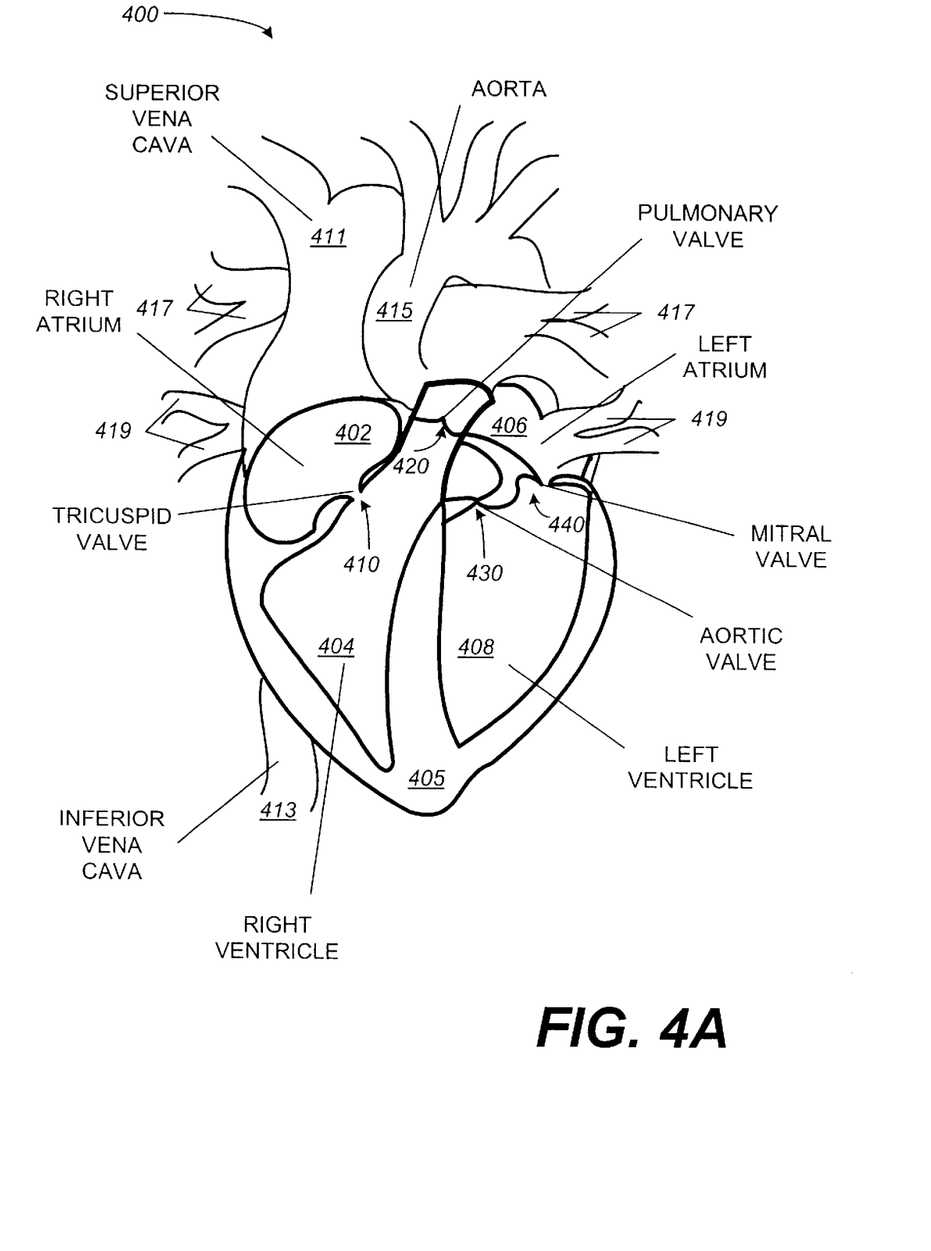
FIGS. 4A–4B along with FIGS. 5A–5C illustrate the effect of stenosis on blood flow through the heart and lungs of a patient perfused with a contrast agent.
Figure 4B:
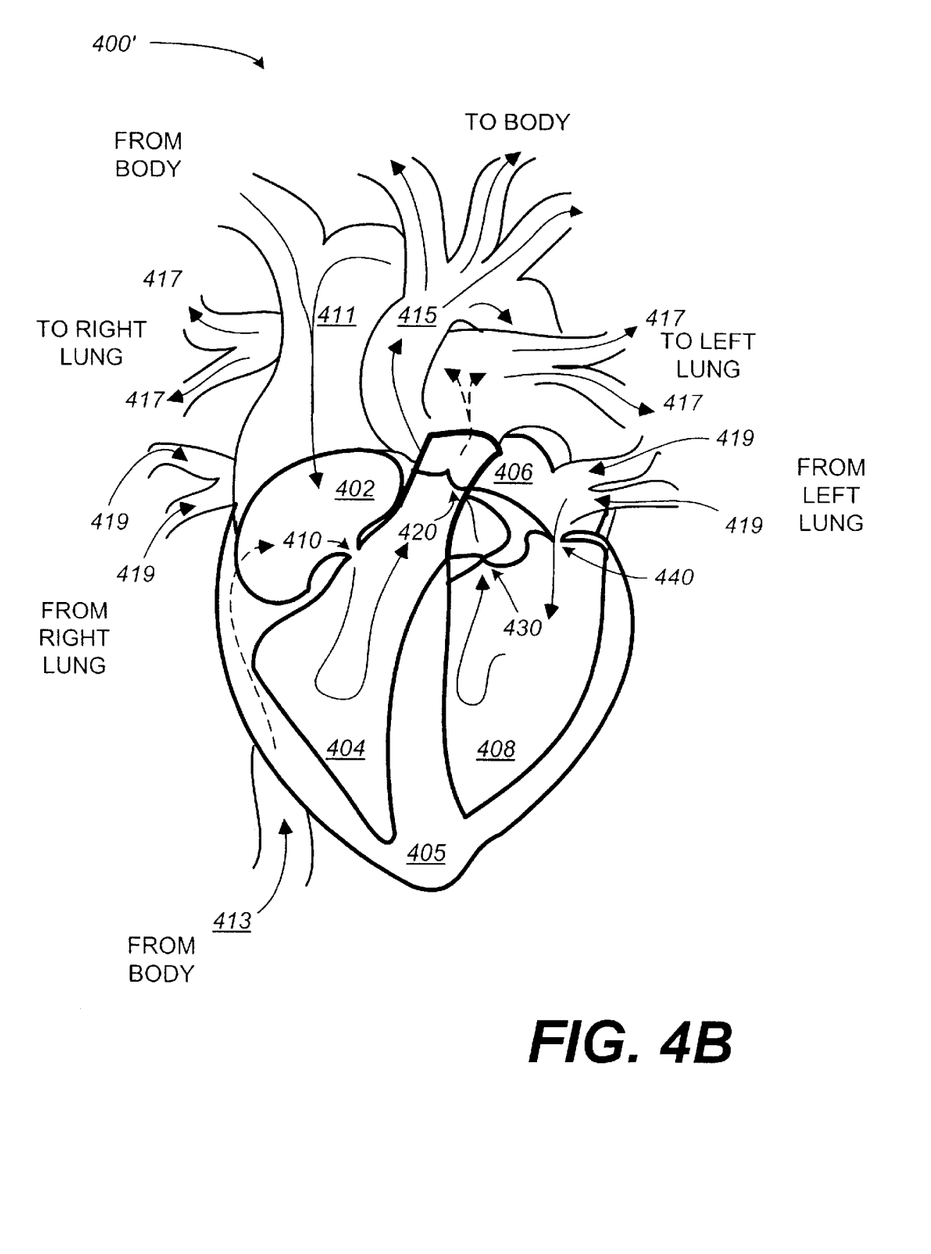

Having described the relative relationships between the various structures and interconnections of the human heart as illustrated in FIG. 4A, reference is now directed to FIG. 4B. In this regard, FIG. 4B illustrates blood flow into, through, and out from the heart 400'. Blood from the body flows into the right atrium 402 via the inferior and the superior vena cava 413, 411 respectively. After the tricuspid valve 410 opens, blood from the right atrium 402 flows past the tricuspid valve 410 into the right ventricle 404. After the pulmonary valve 420 opens, blood in the right ventricle 404 is expelled from the heart and transferred to the right and left lungs (not shown) via the pulmonary arteries 417. After the blood has been oxygenated in the right and left lungs (not shown), the blood is returned via the pulmonary veins 419 to the left atrium 406. After the mitral valve 440 opens, the oxygenated blood flows from the left atrium 406 to the left ventricle 408. Upon opening of the aortic valve 430, blood is expelled from the heart 400' by the left ventricle 408 and is carried by the aorta 415 on its way to the various parts of the body.

When a contrast agent has been introduced into the bloodstream, a significant quantity of the contrast agent will be contained within the right and left atrium 402, 406 respectively, as well as, the right and left ventricles 404, 408 of the heart 400', while only a relatively smaller quantity of contrast agent will enter tissues or organs by way of capillaries within the circulatory system. In this way, the introduction of a contrast agent into the bloodstream followed by ultrasound insonification permits imaging of the blood flow through the heart for a period of time until the contrast agent has perfused the myocardial tissue layer 405.

Figure 5A:
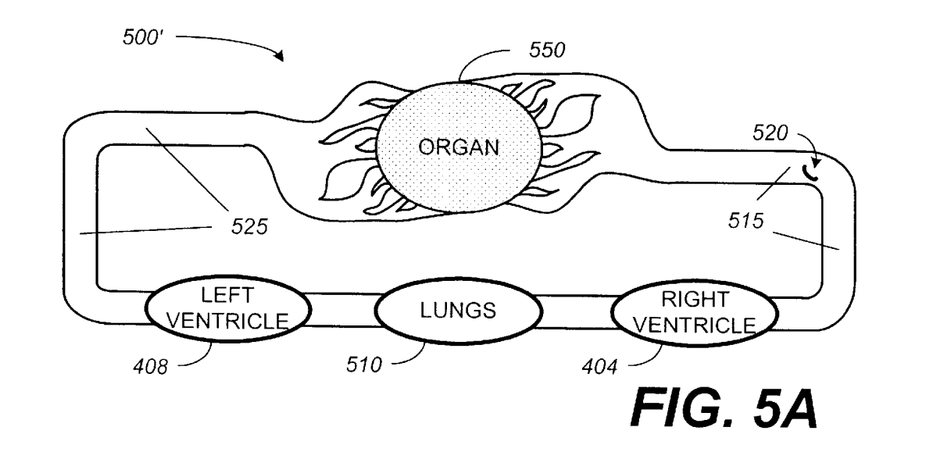
Figure 5B:
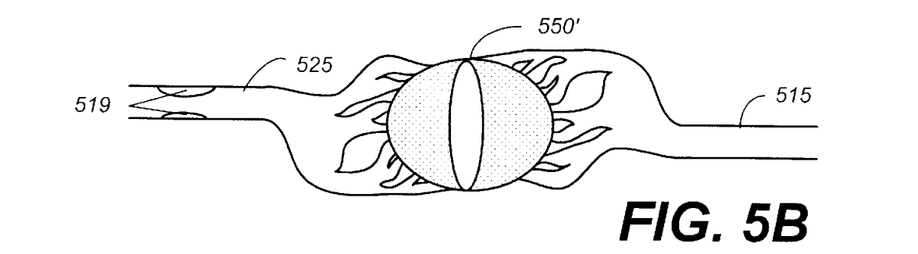
Figure 5C:
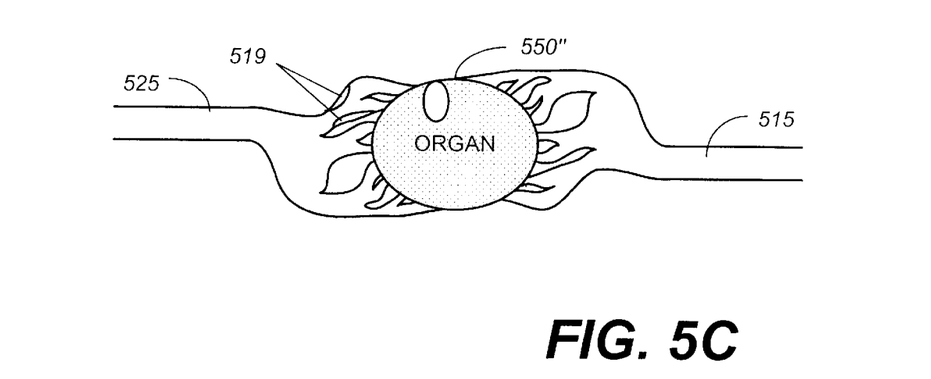

Having described operation of the heart 400, 400' with regard to the illustrations of FIGS. 4A and 4B, reference is now directed to FIGS. 5A through 5C, which illustrate measurement of the rate of perfusion of an organ or area of the body that may be performed by the UCATI system 150 of FIG. 2A. In this regard, FIG. 5A illustrates the travel of a contrast agent infused into the bloodstream of a patient via an intravenous injection site 520 through an organ of interest 550. As previously described in relation to FIGS. 4A and 4B, operation of the heart 400, 400' promotes blood circulation from the intravenous injection site 520 in a clockwise direction across the structures illustrated in FIG. 5A. Proceeding in a clockwise fashion from the intravenous injection site 520 located in one of the various veins 515 (one shown for simplicity of illustration), blood traverses the right ventricle 404 on its way to the lungs 510. Blood is returned from the lungs 510 to the heart 400 (not shown in total) where it passes from the left ventricle 408 out to the various parts of the body through the various arteries of the body 525 (one shown for simplicity of illustration). The perfusion rate into the organ of interest 550 can be used to evaluate the viability of blood flow through the organ of interest 550 or to identify the location of a stenosis. As further illustrated in FIG. 5B, if a stenosis 519 is located within an artery 525 that supplies blood to organ of interest 550', the rate of expected perfusion across the various capillaries (not shown) of the organ of interest 550' will be slowed across the entire organ of interest 550'. On the other hand, as is illustrated with regard to FIG. 5C, if the stenosis 519 is located within an artery 525 that feeds a portion of the organ of interest 550" the rate of expected perfusion will be slowed across a small portion of the organ of interest 550".

The method for ultrasonic imaging 200 of the present invention can be implemented via a combination of hardware, firmware, and software. In the preferred embodiment, the method for ultrasonic imaging 200 is implemented in hardware, software, or firmware that is stored in a memory and that is executed by a suitable instruction execution system. If implemented in hardware, as in an alternative embodiment, the method for ultrasonic imaging 200 can implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The method for ultrasonic imaging 200, which comprises an ordered listing of executable instructions for implementing logical functions, can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

What is claimed is:

1. A method for non-linear ultrasonic response signal detection, comprising:
    introducing at least one contrast agent into tissue targeted for imaging;
    insonifying the tissue with a plurality of pressure waveforms to generate a plurality of corresponding responses;
    measuring each of the plurality of corresponding responses to the plurality of pressure waveforms focusing only at a fundamental frequency;
    generating a projected response from a mathematical combination of a first subset of the plurality of responses;
    generating a measured response from a second subset of the plurality of responses; and
    mathematically manipulating the projected response and the measured response to derive the non-linear response.

2. The method of claim 1, wherein the step of insonifying is performed by:
    transmitting a plurality of subsets of pressure waves each subset having a different phase.

3. The method of claim 1, wherein the step of insonifying is performed by:
    transmitting a plurality of pressure waves having substantially the same envelope shape and frequency content.

4. The method of claim 1, wherein the step of insonifying is performed by:
    transmitting a plurality of pressure waves that are scaled in magnitude.

5. The method of claim 4, wherein pressure wave scaling is accomplished by firing a subset of available transducer elements.

6. The method of claim 4, wherein pressure wave scaling is accomplished by:
    firing a first subset of transducer elements to generate the first pressure wave; and
    firing a second subset of transducer elements to generate the second pressure wave, wherein the second subset of transducer elements overlaps the first subset of transducer elements.

7. The method of claim 4, wherein pressure wave scaling is accomplished by:
    firing a first subset of transducer elements to generate a first pressure wave;
    firing a second subset of transducer elements to generate a second pressure wave; and
    firing a third subset of transducer elements to generate a third pressure wave, wherein the sum of the magnitudes from both the first and the third pressure waves is substantially equivalent with the second pressure wave.

8. The method of claim 1, wherein the step of measuring each of the plurality of corresponding responses is performed with a transducer having a bandwidth less than 60%.

9. The method of claim 1, wherein the step of mathematically manipulating the projected and the measured responses is performed by subtracting the projected response from the measured response.

10. The method of claim 1, wherein the plurality of pressure waves have varying phase and the step of mathematically manipulating the projected and the measured responses is performed by adding a projected response to the measured response.

11. The method of claim 1, wherein the plurality of pressure waves have varying phase and the step of mathematically manipulating the projected and the measured responses is performed by subtracting one of the projected and measured responses from the remaining response.

12. The method of claim 10, further comprising:
    adjusting the phase of one of the projected and measured responses prior to performing the step of mathematically manipulating.

13. The method of claim 11, further comprising:
    adjusting the phase of one of the projected and measured responses prior to performing the step of mathematically manipulating.

14. The method of claim 10, further comprising:
    scaling the projected response in relation to the magnitude of each of the respective transmitted pressure waves.

15. The method of claim 11, further comprising:
scaling the projected response in relation to the magnitude of each of the respective transmitted pressure waves.

16. The method of claim 1, wherein the step of insonifying the tissue does not result in destruction of the at least one contrast agent.

17. The method of claim 1, wherein the step of measuring is accomplished with a transducer having a response bandwidth centered about the fundamental frequency.

18. The method of claim 1, wherein the plurality of transmitted pressure waveforms have a mechanical index from 0.05 to 0.5.

19. The method of claim 1, further comprising:
insonifying the tissue with a third pressure wave having a fundamental frequency, a shape, and an intensity substantially the same as the first pressure wave;
measuring a third response to the third pressure wave at the fundamental frequency; and
replacing the step of generating a projected response from the first response with generating a projected response by mathematically combining the first and third responses.

20. The method of claim 1, wherein a transmitting means performing the step of insonifying the tissue and a receiving means receiving the corresponding responses are matched in one of bandwidth or time domain impulse response.

21. The method of claim 1, wherein the non-linear ultrasonic response signals being detected are at least one of subharmonic, harmonic, and ultraharmonic.

22. A method for non-linear ultrasonic response signal detection, comprising:
introducing at least one contrast agent into tissue targeted for imaging;
insonifying the tissue with a plurality of pressure waveforms to generate a plurality of corresponding responses;
measuring each of the plurality of corresponding responses to the plurality of pressure waveforms focusing only at a fundamental frequency; and
filtering the plurality of corresponding responses to remove linear responses.

23. The method of claim 22, wherein a transmitting means performing the step of insonifying the tissue and a receiving means receiving the corresponding responses are matched in one of bandwidth or time domain impulse response.

24. The method of claim 22, wherein the non-linear ultrasonic response signals being detected are at least one of subharmonic, harmonic, and ultraharmonic.

25. A method for non-linear ultrasonic response signal detection, comprising:
introducing at least one contrast agent into tissue targeted for imaging;
insonifying the tissue with a plurality of pressure waveforms of varying phase to generate a plurality of corresponding responses;
measuring each of the plurality of corresponding responses to the plurality of pressure waveforms at a fundamental frequency;
generating a projected response from a mathematical combination of a first subset of the plurality of responses;
generating a measured response from a second subset of the plurality of responses; and
mathematically manipulating the projected response and the measured response to derive the non-linear response by adding the projected response to the measure response.

26. The method of claim 25, wherein a transmitting means performing the step of insonifying the tissue and a receiving means receiving the corresponding responses are matched in one of bandwidth or time domain impulse response.

27. The method of claim 25, wherein the non-linear ultrasonic response signals being detected are at least one of subharmonic, harmonic, and ultraharmonic.

28. A method for non-linear ultrasonic response signal detection, comprising:
introducing at least one contrast agent into tissue targeted for imaging;
insonifying the tissue with a plurality of pressure waveforms to generate a plurality of corresponding responses, wherein said step of insonifying does not result in destruction of the at least one contrast agent;
measuring each of the plurality of corresponding responses to the plurality of pressure waveforms at a fundamental frequency;
generating a projected response from a mathematical combination of a first subset of the plurality of responses;
generating a measured response from a second subset of the plurality of responses; and
mathematically manipulating the projected response and the measured response to derive the non-linear response.

29. The method of claim 28, wherein a transmitting means performing the step of insonifying the tissue and a receiving means receiving the corresponding responses are matched in one of bandwidth or time domain impulse response.

30. The method of claim 28, wherein the non-linear ultrasonic response signals being detected are at least one of subharmonic, harmonic, and ultraharmonic.

31. A method for non-linear ultrasonic response signal detection, comprising:
introducing at least one contrast agent into tissue targeted for imaging;
insonifying the tissue with a plurality of pressure waveforms having a mechanical index from 0.05 to 0.5 to generate a plurality of corresponding responses;
measuring each of the plurality of corresponding responses to the plurality of pressure waveforms at a fundamental frequency;
generating a projected response from a mathematical combination of a first subset of the plurality of responses;
generating a measured response from a second subset of the plurality of responses; and
mathematically manipulating the projected response and the measured response to derive the non-linear response.

32. The method of claim 31, wherein a transmitting means performing the step of insonifying the tissue and a receiving means receiving the corresponding responses are matched in one of bandwidth or time domain impulse response.

33. The method of claim 31, wherein the non-linear ultrasonic response signals being detected are at least one of subharmonic, harmonic, and ultraharmonic.

* * * * *